United States Patent
Tormoen et al.

(10) Patent No.: US 8,623,185 B2
(45) Date of Patent: Jan. 7, 2014

(54) PLANAR MULTI-ELECTRODE ARRAY SENSOR FOR LOCALIZED ELECTROCHEMICAL CORROSION DETECTION

(75) Inventors: Garth William Tormoen, Portland, OR (US); Christopher Sean Brossia, Dublin, OH (US)

(73) Assignee: Southwest Research Institute, San Antonio, TX (US)

( * ) Notice: Subject to any disclaimer, the term of this patent is extended or adjusted under 35 U.S.C. 154(b) by 1050 days.

(21) Appl. No.: 11/548,949

(22) Filed: Oct. 12, 2006

(65) Prior Publication Data

US 2007/0193887 A1 Aug. 23, 2007

Related U.S. Application Data

(60) Provisional application No. 60/726,076, filed on Oct. 12, 2005.

(51) Int. Cl.
*G01N 27/26* (2006.01)

(52) U.S. Cl.
USPC ......... 204/404; 324/693; 324/700; 205/775.5

(58) Field of Classification Search
USPC ........................ 204/404; 324/700; 205/775.5
See application file for complete search history.

(56) References Cited

U.S. PATENT DOCUMENTS

| | | | |
|---|---|---|---|
| 5,338,432 A * | 8/1994 | Agarwala et al. | 205/118 |
| 5,437,773 A | 8/1995 | Glass et al. | 204/153.11 |
| 5,755,230 A | 5/1998 | Schmidt et al. | 128/731 |
| 5,830,343 A | 11/1998 | Hintsche et al. | 205/775 |
| 6,132,593 A | 10/2000 | Tan | 205/776.5 |
| 6,383,451 B1 | 5/2002 | Kim et al. | 422/53 |
| 6,420,867 B1 | 7/2002 | Goldfine et al. | 324/242 |
| 6,683,446 B1 * | 1/2004 | Pope et al. | 324/71.1 |
| 6,683,463 B2 | 1/2004 | Yang et al. | 324/700 |
| 6,690,182 B2 * | 2/2004 | Kelly et al. | 324/700 |
| 6,730,212 B1 | 5/2004 | Yamagishi et al. | 205/777.5 |
| 6,902,661 B2 | 6/2005 | Thomas, III et al. | 205/776.5 |
| 6,935,425 B2 | 8/2005 | Aronstam | 166/250.11 |
| 6,937,002 B2 | 8/2005 | Pope et al. | 324/71.1 |
| 6,960,476 B2 | 11/2005 | Morris | 436/149 |
| 7,063,781 B2 * | 6/2006 | Murray et al. | 205/789 |
| 2003/0029232 A1 | 2/2003 | Felix et al. | 73/86 |
| 2003/0085136 A1 * | 5/2003 | Marchal et al. | 205/775.5 |

OTHER PUBLICATIONS

International Search Report and Written Opinion for International Application No. PCT/US06/39937 (11 pages), Apr. 10, 2007.
Martinez, "New Multilayer Thin-Film Sensors Enable Fast, Efficient Monitoring of Aircraft Defects", Roadrunner, p. 4, 2006.
Deffenbaugh, "Valve Will Help Gas Industry Save Maintenance Costs, Software Program Can Predict Corrosion in Alloys", 2007 R&D 100 Winners, pp. 4-5, 2007.
International Preliminary Report on Patentability PCT/US2006/039937, 9 pages, Apr. 24, 2008.

* cited by examiner

*Primary Examiner* — Bach Dinh
(74) *Attorney, Agent, or Firm* — Chowdhury & Georgakis PC; Ann C. Livingston

(57) ABSTRACT

A planarized type of coupled multi-electrode corrosion sensing device. Electrode pads are fabricated on a thin backing, such as a thin film. Each pad has an associated electrical lead for connection to auxiliary electronic circuitry, which may include a resistor associated with each electrical pad. The design permits the device to be easily placed in small crevices or under coatings such as paint.

6 Claims, 2 Drawing Sheets

PLANAR MULTI-ELECTRODE ARRAY SENSOR FOR LOCALIZED ELECTROCHEMICAL CORROSION DETECTION

RELATED PATENT APPLICATION

This application claims the benefit of U.S. Provisional Application No. 60/726,076, filed Oct. 12, 2005 and entitled "Planar Multi-Electrode Array Sensor For Localized Electrochemical Corrosion Detection."

GOVERNMENT LICENSE RIGHTS

The U.S. Government has a paid-up license in this invention and the right in certain circumstances to require the patent owner to license others on reasonable terms as provided for by the terms of the United States Department of Energy Contract No. DE-FC26-04NT42267.

TECHNICAL FIELD OF THE INVENTION

This invention relates to sensors for detecting corrosion in electrically conductive materials, and more particularly to a multi-electrode sensor fabricated in thin-film form.

BACKGROUND OF THE INVENTION

Corrosion is a natural process, and at the molecular level, involves a metal atom M being oxidized. The atom loses one or more electrons and leaves the bulk metal, $M \rightarrow M^{m+} + me^-$. The lost electrons are conducted through the bulk metal to another site where they reduce (i.e. combine with) a reducible species such as a dissolved gas or a positively charged ion $G^+$ that is in contact with the bulk metal, $N + ne^- \rightarrow N^{n-}$ and $G^{m+} + me^- \rightarrow G$.

The site where metal atoms lose electrons is called the anode, and the site where electrons are transferred to the reducible species is called the cathode. These sites can be located close to each other on the metal's surface, or far apart depending on the circumstances. When the anodic and cathodic sites are continuous, the corrosion is more or less uniform across the surface. When these sites are far apart, the anodic sites corrode locally.

A corrosion path is essentially an electric circuit, because there is a flow of current between the cathode and anode sites. In order for a current to flow, Kirchoff's circuit laws require that a circuit be closed and that there exists a driving potential (voltage). Part of the corrosion circuit is the base metal itself; the rest of the circuit exists in an external conductive solution (i.e. an electrolyte) in contact with the metal. This electrolyte takes away the oxidized metal ions from the anode and provides a reduction species (either nonmetalic atoms or metallic ions) to the cathode. Both the cathode and anode sites are immersed in an electrolyte for the corrosion circuit to be complete.

In corroding systems, potential gradients can be created by a number of mechanisms. These include differences in the free energy or the related electrochemical potentials for different reactions and gradients in the concentration of charged species in the solution. When two electrodes exhibiting differing potentials are electrically connected, a current flows in the external circuit.

There are various approaches to monitoring corrosion. Electrochemical approaches rely on the above-described electrochemical corrosion principles and the measurement of potentials or currents to monitor corrosion damage.

An emerging corrosion monitoring technology makes use of multi-electrode array sensors. Examples of such sensors are described in U.S. Pat. No. 6,132,593 to Tan, entitled "Method and Apparatus for Measuring Localized Corrosion and Other Heterogeneous Electrochemical Processes", and in U.S. Pat. No. 6,683,463 to L. Yang, entitled "Sensor Array for Electrochemical Corrosion Monitoring". These arrays may be used to study spatio-temporal patterns at corrosion sites on metals.

DETAILED DESCRIPTION OF THE INVENTION

The following description is directed to a "coupled multi-electrode array sensor", fabricated using techniques that result in a planarized sensor design. In other words, as compared to other multi-electrode sensor designs, the electrodes and leads are approximately planar, a result of being fabricated "bottom up" upon the same backing.

The design facilitates use of the sensor under paint or other coatings or under insulation, to detect corrosion of a metal surface under paint or some other type of coating, as well as in occluded regions (crevices) previously unreachable by coupled multielectrode array sensors. For purposes of this description, the sensor is described as being located in a "subsurface", which means a location that is under or in a coating or under some other type of overlying material.

An advantage of the invention is that corrosion under a coating can be detected without the need to strip the coating. The sensor can be embedded under the coating to reliably measure the corrosion rate, and to provide early warning of corrosion. The design of the sensor excludes the need to penetrate a coating to measure corrosion, and when attached to the appropriate electronics, the sensor may transmit real time corrosion rate signals, via a non contact (wireless) signal, such as a radio frequency signal. The use of the sensor saves time in detecting corrosion problems. It also provides real time assessment of structural integrity so that maintenance can be scheduled before breakdowns occur.

Corrosion monitoring of a particular structure can be done using one or more sensors at strategically placed locations in conjunction with a variety of receiver types. Various examples of receivers are a hand held monitoring device, a device on-board a vehicle whose metallic structure is being monitored, or a remote monitoring station.

A feature of localized corrosion under coatings is that it occurs in isolated areas. It often consists of areas of small lateral dimension compared to depth. The sensor described herein is particularly suited for this type of detection. Unlike galvanic sensors, it need not operate at an electrochemical potential that is raised relative to the corrosion condition under paint or other coatings.

Figure 1:
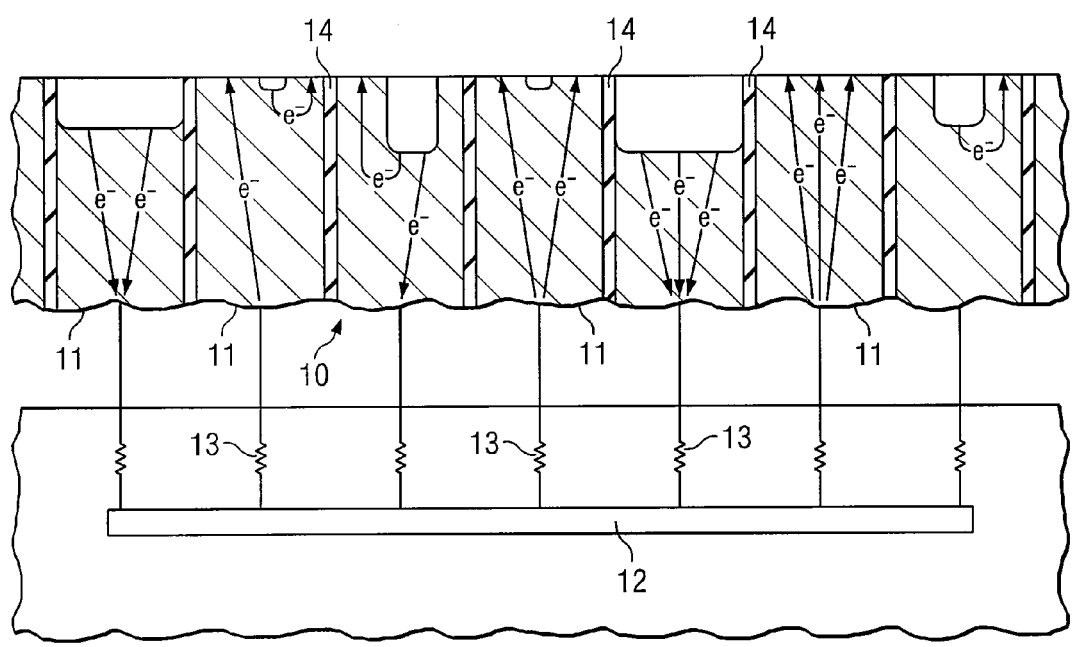
FIG. 1 illustrates the principle of operation of a coupled multi-electrode sensor.

FIG. 1 illustrates the basic principle of operation of a coupled multi-electrode sensor 10. Sensor 10 is a "wire electrode" type sensor, such as those described in the patents referenced in the Background.

Multiple sensing electrodes 11 are typically made from the same material as used for a given test material, that is, the material whose corrosion (or other electrochemical process) is of interest. At least a portion of a surface of each electrode 11 is exposed to the corrosion. The electrodes 11 are electrically isolated from each other by an insulating material 14.

The electrodes 11 are connected to a common node (coupling joint 12) through resistors 13. Each electrode 11 is connected to an associated resistor 13. As explained below, the electrical circuitry (including resistors 13 and their common coupling node 12) is used with additional instrumentation to measure the electrical activity to an from the electrodes 12.

When a metal undergoes non-uniform (heterogeneous) corrosion, particularly localized corrosion such as pitting corrosion or crevice corrosion, electrons are released from the anodic sites where the metal corrodes and travel to the cathodic sites where the metal corrodes less or does not corrode.

In a coupled multi-electrode sensor, there are multiple miniature electrodes. Statistically, some of the electrodes have properties like the anodic sites and others have properties like the cathodic sites of the corroding metal. When the electrodes are electrically isolated from each other but coupled together by connecting each of them to a common joint through an external circuit, the electrodes with anodic properties simulate the anodic areas, and the electrodes with cathodic properties simulate the cathodic areas of the corroding metal. Electrons released from the anodic electrodes are forced to flow through the external circuit to the cathodic electrodes. Thus, anodic currents flow into the more corroding electrodes, and cathodic currents flow out of the less corroding or non-corroding electrodes. The resulting electrical currents are measured, and the localized or non-uniform corrosion rates are determined by an appropriately programmed analyzer.

Using a coupled multi-electrode sensor, such as sensor 10, corrosion sensing directly measures actual corrosion in real time. The corrosion phenomena triggers the currents; no external electrical stimuli is required. The electrical activity between electrodes is monitored, rather than actively probed.

Figure 2:
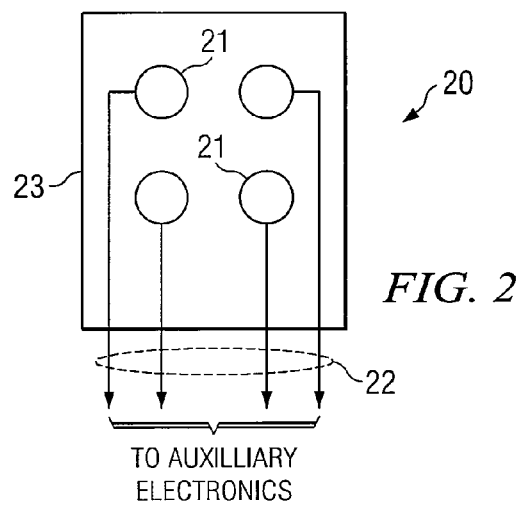
FIG. 2 illustrates a planarized multi-electrode sensor in accordance with the invention.

FIG. 2 illustrates a planarized coupled multi-electrode sensor 20 in accordance with the invention. As explained below, sensor 20 is planarized in the sense that its electrode surfaces and their electrical connections are approximately planar. However, the principles of operation are the same as for the generalized description of the coupled multi-electrode sensor 10 of FIG. 1. Each electrode is structurally identical, so that the measured electrical responses of the electrodes can be easily compared and analyzed.

In the example of FIG. 2, sensor 20 has four electrode pads 21 fabricated upon a thin backing 23 in a square pattern. However, in other embodiments, there may be any number of electrode pads 21 in any arbitrary or geometric pattern. An electrical lead 22 connects each pad 21 to auxiliary electronic circuitry, such as described below in connection with FIG. 3. As described above, the pads 21 and electrodes 22 permit sensor 20 to simulate a single metal electrode for corrosion monitoring purposes.

Backing 23 may be a thin film material, with an example of a suitable material being a polymer. Typical characteristics of backing 23 are that it is flexible, non electrically conductive, and chemically inert. A specific example of a suitable thin film backing 23 is a polyimide, such as the KAPTON® polyimide manufactured by E.I. duPont de Nemours and Company.

Typically, electrodes 21 are fabricated from material similar to the material whose corrosion is being monitored. Examples of such materials are iron, aluminum, magnesium, and their alloys. For example, for monitoring a carbon steel structure, electrode pads 21 would be made from carbon steel. In some situations, it may be appropriate to use a material that is analogous to the material of interest, or any material at all, in the sense that the electrical activity between electrodes will provide the desired information about the electrochemical environment, regardless of the particular composition of the electrodes.

Electrode pads 21 may be disk-shaped, but other pad geometries are possible. Electrode pads 21 may be made in geometries as small as 100 micrometers in thickness or even smaller, which facilitates placement of the sensor into small crevices.

Where backing 23 is a thin film, electrodes 21 may be deposited using thin film deposition techniques, such as evaporation or sputtering, used for depositing metals as thin films. Alternatively, the electrode pads 21 and/or leads 22 may be machined or otherwise formed from a larger piece of material, then attached to the substrate 23. The attachment of pads 21 to leads 22, if separately fabricated, may be by means of a conductive epoxy.

As an alternative to a thin film, backing 23 may be made from a more rigid substrate material such as a silicon or ceramic material. In the case of a silicon backing material, conventional fabrication techniques such as those used for the manufacture of integrated circuits could be used for substrate formation (for backing 23), and for patterning and deposition of the electrodes 21 and leads 22.

As illustrated, the circuit layout of sensor 20 has an electrical lead 22 to be made to each electrode 21. These leads 22 are electrically insulated from each other by being non touching and by being separated by a non conductive material. In the embodiment of FIG. 2, these leads 22 are "on-chip" in the sense that they are on the same backing as the electrodes. Leads 22 extend to the perimeter of the array to permit connection to external electrical leads, which in turn, permit electrical activity between the electrode pads 21 to be monitored.

In general, electrodes and/or leads 22 may be fabricated in or on backing 23 in any number of ways. However, as explained below, regardless of the fabrication method, eventually at least a portion of each electrode pad 21 is exposed to the corrosion environment.

The electrical leads 22 are insulated from the environment being monitored. This eliminates galvanic corrosion and maintains electrical integrity of the sensor 20. As an example of suitable insulation, sensor 20 could be coated with or embedded or sealed in a non conductive material, with only pads 21 exposed to the environment.

Figure 3:
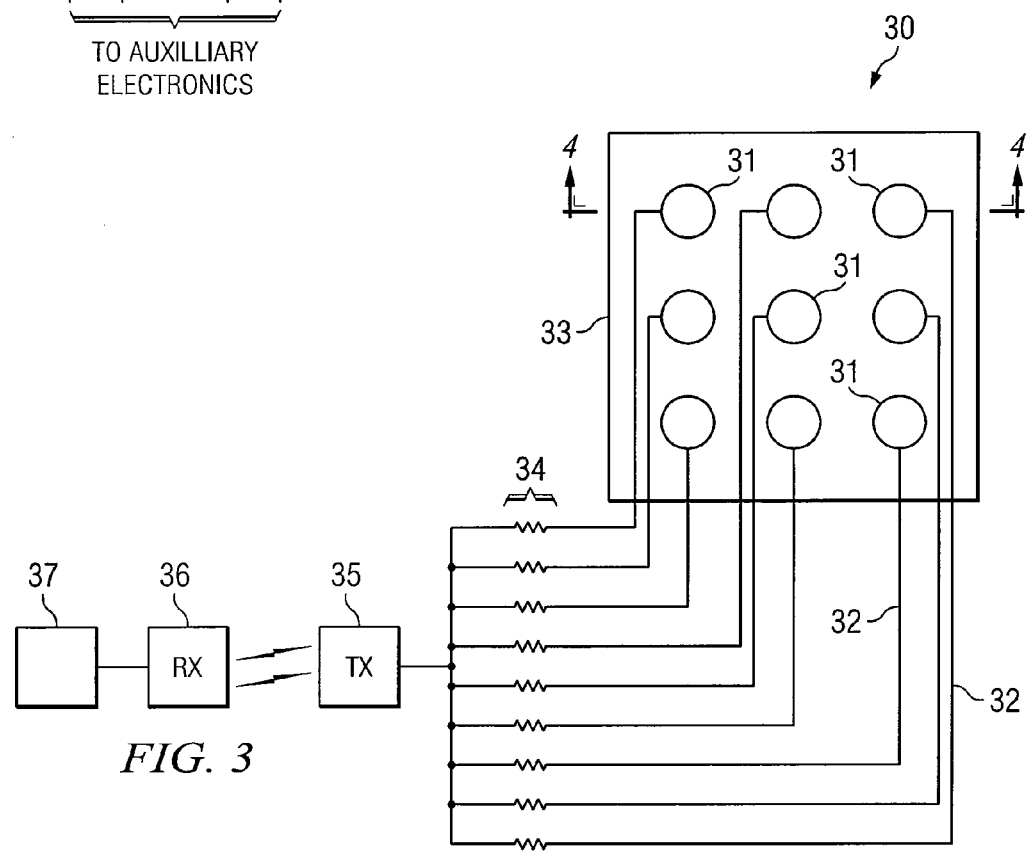
FIG. 3 illustrates another example of a planarized multi-electrode sensor, and further illustrates additional electronic circuitry associated with the sensor.
Figure 4:
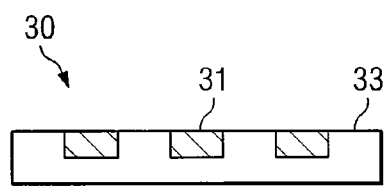
FIG. 4 is a side view of the sensor of FIG. 3.

FIGS. 3 and 4 illustrate another example of a thin film sensor 30. FIG. 3 is a plan view, and FIG. 4 is a side view. In the example of FIGS. 3 and 4, there are six electrode pads 31, each having an associated lead 32.

As in the case of sensor 20, sensor 30 has electrode pads 31 and leads 32 fabricated upon, or attached to, a thin film or other planar backing 33. At least a portion of each pad 31 is exposed to the corrosive environment.

In FIG. 3, the sensor 30 is shown as being "wired-out" to resistors 34 between the electrodes 31. As explained above, quantitative measurements are taken by measuring the voltage across resistors 34. Resistors 34 are electrically connected to a common node, which is then electrically connected to a transmitter 35.

FIG. 3 illustrates resistors 34 and transmitter 35 as not being attached to backing 33. However, in various embodiments, resistors 34 and/or transmitter 35 may be physically integrated parts of sensor 30 or may be physically separate components. For example, resistors 34 could be fabricated on backing 33 as an integrated circuit with leads 32.

Transmitter 35 communicates wirelessly to a receiver 36, which is part of a larger processor-based corrosion analyzer 37. The communications between transmitter 35 and receiver 36 could be implemented with known RF communications techniques. An advantage of connecting the leads through resistors is that the transmitted signals represent voltages across the resistors associated with the electrodes. In various embodiments, a voltmeter or ammeter could be used to measure electrical activity, as discussed in the patents referenced in the Background.

Corrosion analyzer 37 can be a desktop type system, or it can be a handheld device. For example, a mini-controller or PDA type device with a wireless modem could be programmed to receive signals from the sensor and to analyze the signals.

FIG. 4 is a side view of sensor 30, illustrating its flat (planar) design. The actual thickness can be 100 micrometers or less. This thin dimension permits sensor 30 to be inserted into crevices and other small spaces, and facilitates its placement under paints and other coatings. A typical size of sensor 30 is 1×1 centimeter.

The design of sensors 20 and 30 (and other variations) permits the electronic circuitry to be miniaturized and integrated into the thin film package. This facilitates embedding of the sensor under coatings such as paint, with transmission of a signal representing corrosion to a remote receiver via a non-contact method. The high sensitivity of the sensor enables simple, inexpensive, and quick discriminative evaluation of different types of coatings.

The invention claimed is:

1. A method for detecting corrosion using one or more sensors at strategically placed locations, comprising:
    embedding at least one sensor under a paint coating;
    wherein each sensor has: a thin film backing, an array of three or more planar electrodes fabricated on the backing, each electrode having the shape of a closed two-dimensional figure, and each electrode having its own electrical lead for electrically connecting each electrode, via a common node, to auxiliary measurement circuitry that has at least a transmitter;
    wherein each electrode has a single flat surface area operable to be exposed to the corrosion and each electrode is electrically insulated from other electrodes;
    wherein the electrodes are fabricated in or on the backing such that the entire sensor is planar, that is, the electrodes and backing are within a flat plane, only one surface of the backing exposes the electrodes, and the backing electrically insulates the entire plane other than the non-exposed surfaces of the electrodes;
    wherein the electrical leads are also fabricated in the backing and are planar with the sensor, and are insulated from each other and from the corrosion, and each electrical lead is electrically insulated from all electrodes other than its associated electrode except at the common node;
    wherein each electrode is operable as an anode or cathode depending on the response of the electrode to the corrosion, such that the array becomes a multiplicity of anodes and cathodes;
    wherein each electrode is electrically connected to the common node, such that the sensor simulates a one-piece electrode surface;
    operating the sensor by passively monitoring electrical activity from the electrodes, without applied electrical stimuli to the electrodes, and using a wireless signal from the transmitter that represents electrical activity between the electrodes; and
    interpreting the signal to determine corrosive activity.

2. The method of claim 1, wherein the electrodes are each made from the same material.

3. The method of claim 1, wherein the electrodes are each connected to the common node through a resistor.

4. The method of claim 3, wherein each resistor has the same resistance value.

5. The method of claim 3, wherein the resistors have more than one resistance value.

6. The method of claim 3, wherein the electrodes and resistors are fabricated as a physically integrated device.

* * * * *